United States Patent
Astier et al.

(10) Patent No.: US 10,156,568 B2
(45) Date of Patent: Dec. 18, 2018

(54) IMMUNOASSAY FOR DETECTION OF VIRUS-ANTIBODY NANOCOMPLEXES IN SOLUTION BY CHIP-BASED PILLAR ARRAY

(71) Applicant: International Business Machines Corporation, Armonk, NY (US)

(72) Inventors: Yann Astier, Irvington, NY (US); Stacey M. Gifford, Ridgefield, CT (US); Benjamin H. Wunsch, Mt. Kisco, NY (US)

(73) Assignee: International Business Machines Corporation, Armonk, NY (US)

( * ) Notice: Subject to any disclaimer, the term of this patent is extended or adjusted under 35 U.S.C. 154(b) by 563 days.

(21) Appl. No.: 14/700,939

(22) Filed: Apr. 30, 2015

(65) Prior Publication Data
US 2016/0320389 A1 Nov. 3, 2016

(51) Int. Cl.
*G01N 33/569* (2006.01)
*B01L 3/00* (2006.01)

(52) U.S. Cl.
CPC .. *G01N 33/56983* (2013.01); *B01L 3/502753* (2013.01); *B01L 3/502761* (2013.01); *B01L 2200/0647* (2013.01); *B01L 2200/0652* (2013.01); *G01N 2469/10* (2013.01)

(58) Field of Classification Search
CPC ....... B01L 3/502753; B01L 2200/0652; B01L 2300/0896; B01L 3/502761; B01L 2200/0631; B01L 2300/0864; B01L 2400/086; G01N 2015/0288; G01N 2015/0038; G01N 27/3278; G01N 15/1484; G01N 2015/1081; G01N 30/6095; G01N 33/56983; G01N 2200/0652; G01N 33/491

See application file for complete search history.

(56) References Cited

U.S. PATENT DOCUMENTS

| | | | |
|---|---|---|---|
| 7,169,251 | B2 | 1/2007 | Guo et al. |
| 7,217,562 | B2 | 5/2007 | Cao et al. |
| 7,988,840 | B2 | 8/2011 | Huang et al. |
| 8,232,584 | B2 | 7/2012 | Lieber et al. |

(Continued)

OTHER PUBLICATIONS

N. Boonham et al., "Methods in virus diagnostics: from ELISA to next generation sequencing," Virus Research, vol. 186, Jun. 2014, pp. 20-31.

(Continued)

*Primary Examiner* — Erik B Crawford
(74) *Attorney, Agent, or Firm* — Vazken Alexanian; Michael J. Chang, LLC

(57) ABSTRACT

Techniques for detection of virus-antibody nanocomplexes using a chip-based pillar array are provided. In one aspect, a method for virus detection is provided. The method includes the steps of: collecting a fluid sample from a virus-bearing source; contacting the fluid sample with an antibody that binds to viruses to form a sample-antibody mixture, wherein the antibody is labeled with a fluorescent tag; separating particles including any antibody-virus complexes, if present, from the sample-antibody mixture using an assay nanopillar array; and detecting the antibody-virus complexes, if present, in the particles from the separating step using fluorescence. A virus detection chip device and a chip-based immunoassay method are also provided.

14 Claims, 10 Drawing Sheets

(56) References Cited

U.S. PATENT DOCUMENTS

| | | | |
|---|---|---|---|
| 8,722,423 B2* | 5/2014 | Bergman | B01J 20/28014 436/514 |
| 2005/0089924 A1 | 4/2005 | Ho et al. | |
| 2007/0196820 A1* | 8/2007 | Kapur | B01L 3/502746 435/5 |
| 2007/0254376 A1 | 11/2007 | Wimberger-Friedl et al. | |
| 2007/0269893 A1* | 11/2007 | Blankenstein | B01L 3/502723 436/2 |
| 2009/0208920 A1* | 8/2009 | Ohman | B01L 3/502746 435/2 |
| 2009/0269767 A1* | 10/2009 | Soderlund | B01L 3/50273 435/6.11 |
| 2014/0030788 A1* | 1/2014 | Chen | B01L 3/502707 435/177 |
| 2014/0252505 A1* | 9/2014 | Kobayashi | G01N 15/0656 257/414 |
| 2014/0357527 A1 | 12/2014 | Lindsay et al. | |

OTHER PUBLICATIONS

A.M. Caliendo et al., "Better tests, better care: improved diagnostics for infectious diseases," Clinical Infectious Diseases, vol. 57, No. Suppl 3, Dec. 2013, pp. S139-S170.

V.D. Pham et al., "Production of antibody labeled gold nanoparticles for influenza virus H5N1 diagnosis kit development," Advances in Natural Sciences: Nanoscience and Nanotechnology, vol. 3, No. 4, Dec. 2012, 045017.

P.J. Carney et al., "Flexible label-free quantitative assay for antibodies to influenza virus hemagglutinins," Clinical and Vaccine Immunology, vol. 17, No. 9, Sep. 2010:1407-1416.

A.M. Rossi et al., "Porous silicon biosensor for detection of viruses." Biosensors and Bioelectronics, vol. 23, No. 5, Jul. 2007, pp. 741-745.

F. Patolsky et al., "Electrical detection of single viruses," Proceedings of the National Academy of Sciences of the United States of America, vol. 101, No. 39, Sep. 2004, pp. 14017-14022.

Huang et al., "Continuous Particle Separation Through Deterministic Lateral Displacement," Science, vol. 304 (May 2004).

Inglis, et al., "Critical particle size for fractionation by deterministic lateral displacement," Lab Chip, 6, 655-658 (Mar. 2006).

Loutherback et al., "Improved performance of deterministic lateral displacement arrays with triangular posts," Microfluid Nanofluid 9:1143-1149 (May 2010).

T. Kulrattanarak et al. "Analysis of mixed motion in deterministic rachets via experiment and particle simulation," Microfluid Nanofluid 10:843-853 (2011) (published Oct. 2010).

Wang et al., "Hydrodynamics of Diamond-Shaped Gradient Nanopillar Arrays for Effective DNA translocation into Nanochannels," ACS NANO, vol. 9, No. 2, pp. 1206-1218 (Jan. 2015).

Wang et al., "200 nm Wafer-Scale Integration of Sub-20 nm Sacrificial Nanofluidic Channels for Manipulating and Imaging Single DNA Molecules," 2013 IEEE International Electron Devices Meeting (IEDM) (Dec. 2013).

* cited by examiner

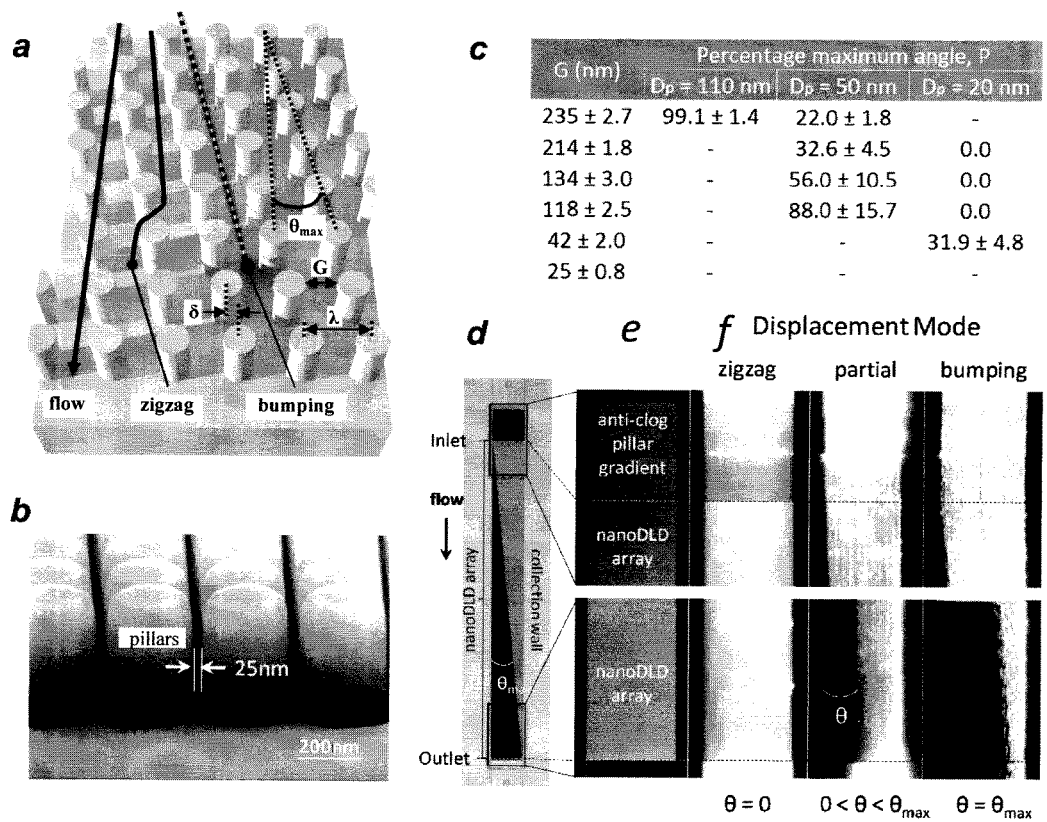
FIGS. 3a-f

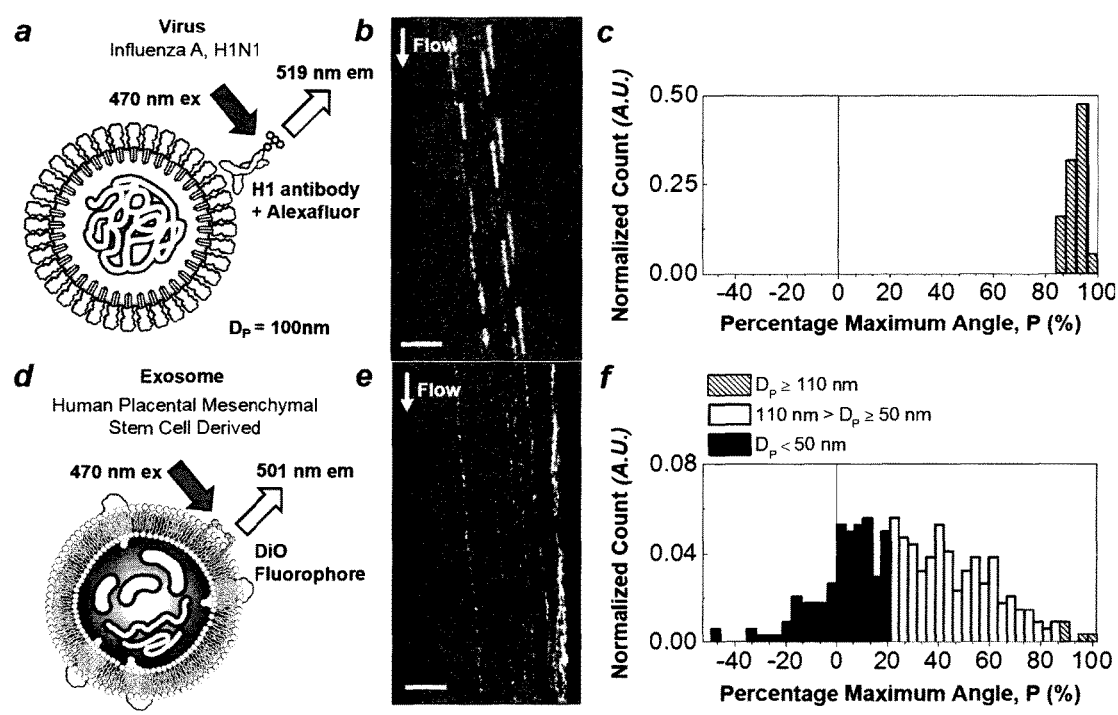
FIGS. 4a-f

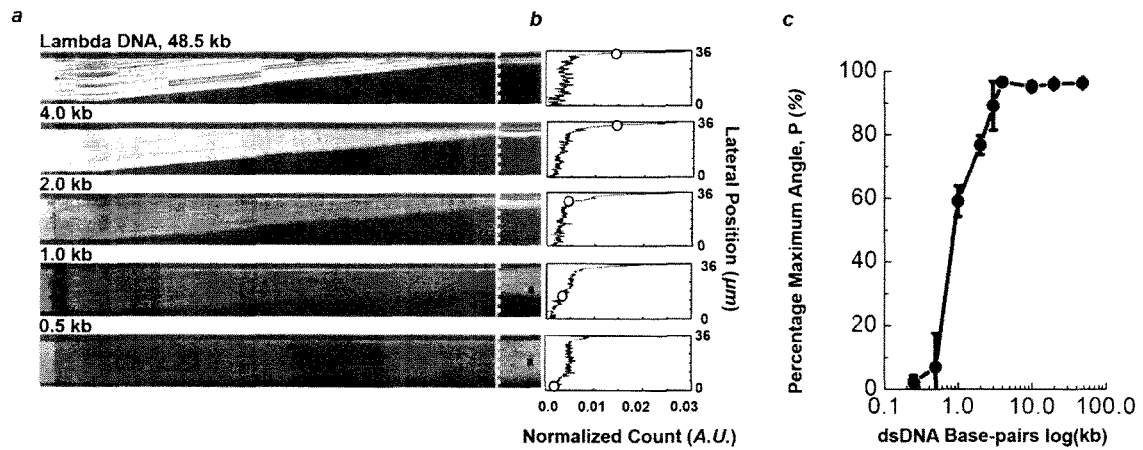
FIGS. 5a-c
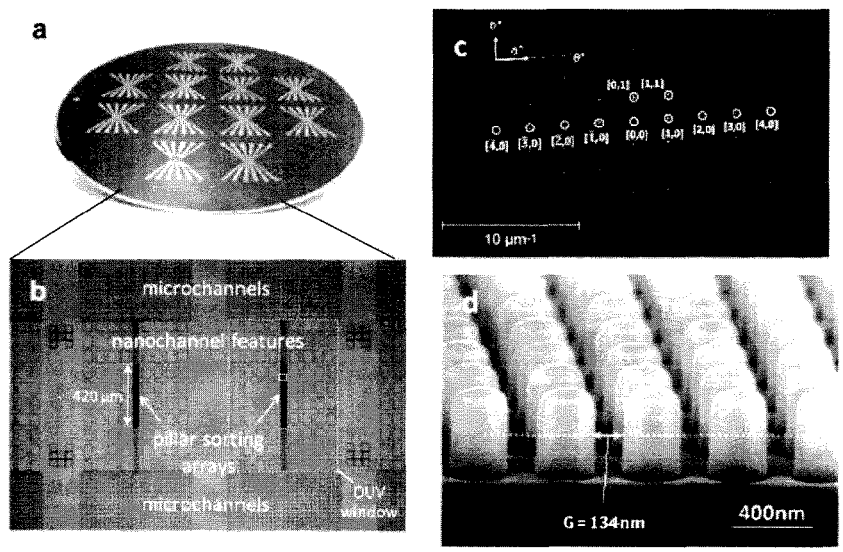
FIGS. 6a-d

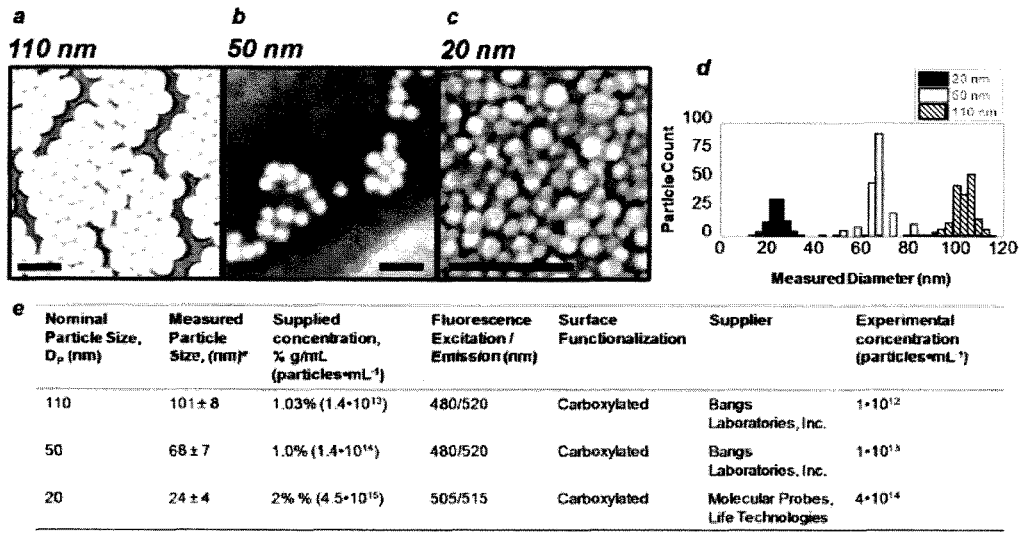
FIGS. 7a-e
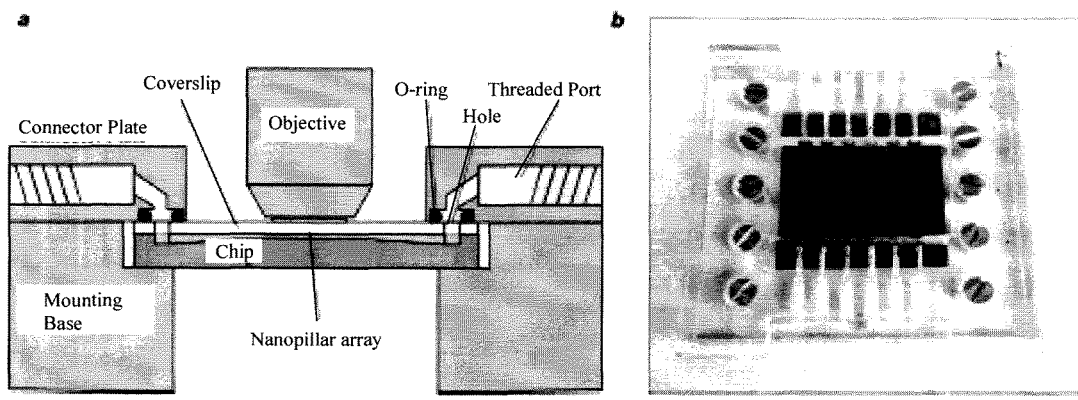
FIGS. 8a-b

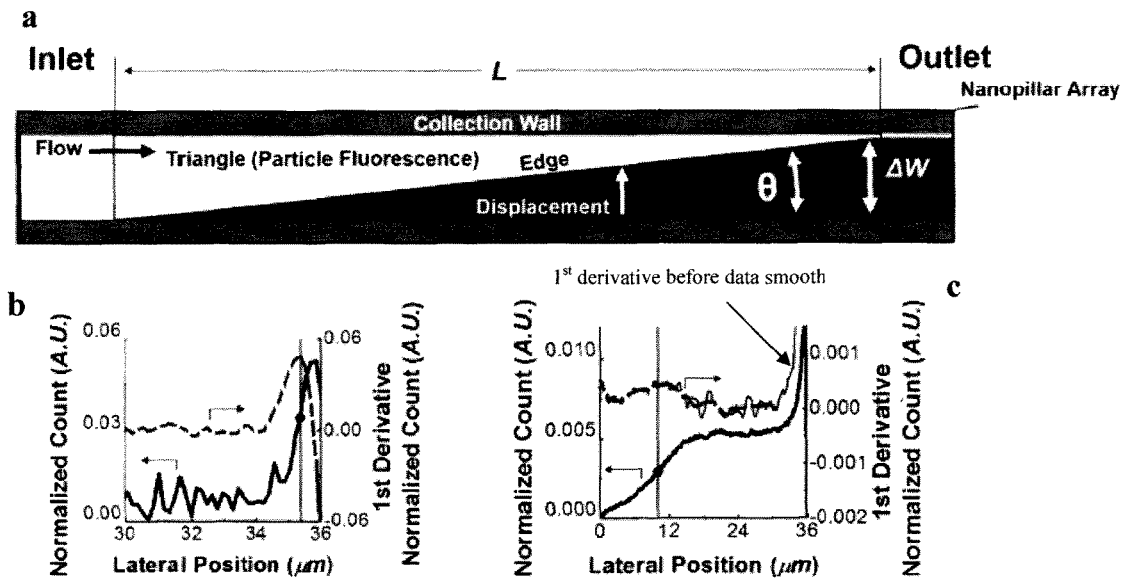
FIGS. 9a-c
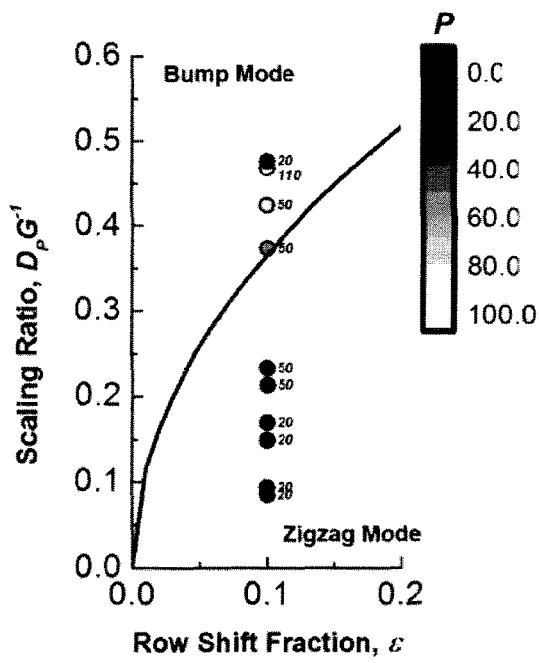
FIG. 10

Performance parameters for nanoDLD displacement of fluorescence polystyrene beads.

| Particle Diameter, $D_p$ (nm) | Array Gap Size, G (nm) | Scaling Ratio $D_p/G$ | Percent Maximum Angle, P (%) | Displacement Efficiency, $\eta$ | Figure of Merit, FOM | Full Displacement Length, $L_C$ (mm) |
|---|---|---|---|---|---|---|
| 110 | 235 | 0.47 | 99.1 ± 1.4 | 99.1% | 0.099 | 0.36 |
| 50 | 235 | 0.21 | 22.0 ± 1.8 | 21.9% | 0.022 | 1.64 |
| 50 | 134 | 0.37 | 32.6 ± 4.5 | 32.5% | 0.032 | 1.11 |
| 50 | 118 | 0.42 | 56.0 ± 10.5 | 55.9% | 0.056 | 0.65 |
| 50 | 42 | 1.19 | 88.0 ± 15.7 | 87.9% | 0.088 | 0.41 |
| 20 | 42 | 0.48 | 31.9 ± 4.8 | 31.8% | 0.032 | 1.13 |

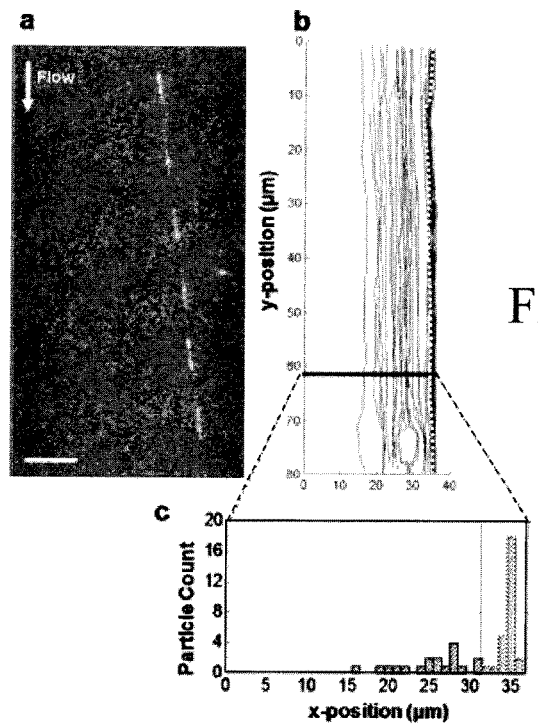
FIGS. 13a-c
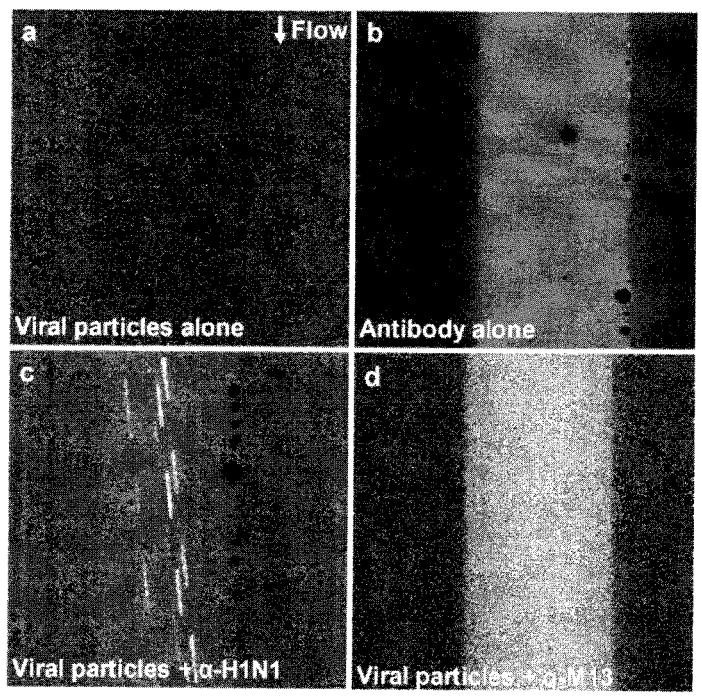
FIGS. 14a-d

End-to-end coil diameters and scaling ratios calculated for dsDNA in nanoDLD displacement experiments.

| Bases (kb) | Length (nm) | De Gennes Coil, $2R_{DG}$ (nm)[a] | $2R_{DG}/G$[a] | Percentage Critical Angle, P (%) |
|---|---|---|---|---|
| 0.25[b] | 85 | - | 0.08 | 2.2 ± 2.1 |
| 0.5[b] | 170 | - | 0.16 | 7.0 ± 10.6 |
| 1.0 | 340 | 74 | 0.31 | 59.1 ± 4.9 |
| 2.0 | 680 | 148 | 0.63 | 76.7 ± 3.0 |
| 3.0 | 1,020 | 221 | 0.94 | 89.1 ± 7.7 |
| 4.0 | 1,360 | 295 | 1.26 | 96.6 ± 0.0 |
| 10.0 | 3,400 | 738 | 3.14 | 95.2 ± 1.4 |
| 20.0 | 6,800 | 1,475 | 6.28 | 96.0 ± 0.7 |
| 48.5 | 16,490 | 3,578 | 15.22 | 96.2 ± 0.4 | a: Calculated with persistence length, $p$ = 50 nm, molecular width, $w$ = 2.4 nm, length per base, $h$ = 0.34 nm and nanochannel width, $D = (GH)^{1/2}$, with nanopillar gap size G = 235 nm, pillar height = 400 nm.
b: These dsDNA molecules have lengths shorter than the smallest nanochannel width, D, and therefore the de Gennes model is not applicable. The coil radius for these strands has not been calculated and is omitted in the table.

FIG. 15

IMMUNOASSAY FOR DETECTION OF VIRUS-ANTIBODY NANOCOMPLEXES IN SOLUTION BY CHIP-BASED PILLAR ARRAY

FIELD OF THE INVENTION

The present invention relates to virus detections, and more particularly, techniques for detection of virus-antibody nanocomplexes using a chip-based pillar array.

BACKGROUND OF THE INVENTION

Viruses replicate and spread through infection of a host organism. For disease-causing viruses, controlling the spread of a viral infection is cause for global concern. Early detection of a viral infection is key to effectively treating infected patients and preventing epidemic spread.

The incubation period for many viruses is on the order of days to weeks and the infection period often begins before symptoms are present. It is therefore often challenging to prevent patient-to-patient infection without sensitive methods to detect viral infection before symptoms appear. Additionally, the effectiveness of many of the available antiviral medications rely on early detection and treatment of disease.

Although technology exists for detection of viral infection, the sensitivity is limited and most rely on sophisticated laboratory equipment and trained technicians. Thus in order to reduce the number of viral infections and improve early treatment, technology is needed for rapid point-of-care viral infection detection by individuals with little medical training.

Current methods for the detection of viral infections in patients rely primarily on "wet" lab techniques, which require an appropriately equipped laboratory and trained staff. Turnaround time for even the most rapid tests is often hours or days, limiting their use as point-of-care viral detection methods. Two commonly used techniques are enzyme-linked immunosorbent assay (ELISA) and polymerase chain reaction (PCR).

ELISA tests detect virus in biological samples through the use of antibodies that bind viral antigens. Viral particles are adhered to a solid surface such as a plastic 96-well plate and are subsequently bound by antibodies that recognize a viral antigen. These primary antibodies or secondary antibodies are covalently linked to a fluorescent molecule or enzyme that produces colorimetric or luminescent signal upon exposure to a ligand. This signal is measured by a fluorimeter or spectrophotometer. ELISA can also be adapted to detect antibodies developed against virus in patient samples, however antibodies against virus are produced later in the infection process.

Although some ELISA methods are considered highly sensitive and can be quantitative, they require expensive laboratory equipment and their reproducibility is dependent on a well-trained technician. They are not suitable for rapid point-of-care detection and often require several hundred microliters of sample. Additionally, there is often disagreement over the numerical cutoff value of the quantified signal leading to potential false positives and false negatives.

PCR and reverse transcription PCR (RT-PCR) detect the nucleic acid component, i.e., deoxyribonucleic acid (DNA) or ribonucleic acid (RNA), of the virus and are generally considered to be more sensitive than ELISA with fewer false positives. PCR uses RNA primers designed to match known sequences in the viral RNA or DNA to amplify fragments which are used as a readout for presence of the virus. PCR and RT-PCR can be quantitative, allowing for accurate calculation of viral load. However, both PCR-based methods require sophisticated and expensive laboratory equipment and trained technicians, eliminating their use as rapid point-of-care tests.

A handful of rapid point-of-care diagnostic tests exist, with the two most widely used being for the detection of human immunodeficiency virus (HIV) and influenza A and B. The advantage of these tests is their ease of use and rapid results, usually in less than 30 minutes. However, the HIV rapid test relies on the detection of antibodies generated by the patient against HIV, which can take several months to reach a detectable level. In line with this, these tests are only qualitative in nature and have been shown to have a high occurrence of false positive and false negative results.

Therefore, there is a need for sensitive, quantitative detection of viral particles in a rapid point-of-care protocol amenable to self-administration with small sample volumes.

SUMMARY OF THE INVENTION

The present invention provides techniques for detection of virus-antibody nanocomplexes using a chip-based pillar array. In one aspect of the invention, a method for virus detection is provided. The method includes the steps of: collecting a fluid sample from a virus-bearing source; contacting the fluid sample with an antibody that binds to viruses to form a sample-antibody mixture, wherein the antibody is labeled with a fluorescent tag; separating particles including any antibody-virus complexes, if present, from the sample-antibody mixture using an assay nanopillar array; and detecting the antibody-virus complexes, if present, in the particles from the separating step using fluorescence.

In another aspect of the invention, a virus detection chip device is provided. The virus detection chip device includes: a capillary opening for accepting a fluid sample collected from a virus-bearing source; a mixing reservoir, connected to the capillary opening, for contacting the fluid sample with an antibody that binds to viruses, wherein the antibody is labeled with a fluorescent tag to form a sample-antibody mixture in cases where the antibody and sample are not pre-mixed; a first filtering nanopillar array, connected to the mixing reservoir, for removing particles from the sample-antibody mixture; a second nanopillar array, connected to the first nanopillar array, for separating particles including any antibody-virus complexes, if present, from the sample-antibody mixture; and a diode-induced fluorescence detector, connected to the second nanopillar array, for detecting the antibody-virus complexes, if present, in the particles using fluorescence.

In yet another aspect of the invention, a chip-based immunoassay method is provided. The method includes the steps of: providing a virus detection chip device having: a capillary opening; a mixing reservoir connected to the capillary opening; a first nanopillar array connected to the mixing reservoir; a second nanopillar array connected to the first nanopillar array; and a diode-induced fluorescence detector connected to the second nanopillar array; introducing a fluid sample collected from a virus-bearing source to the virus detection chip device through the capillary opening; in the mixing reservoir, contacting the fluid sample with an antibody that binds to viruses, wherein the antibody is labeled with a fluorescent tag to form a sample-antibody mixture; removing particles from the sample-antibody mixture using the first nanopillar array; separating particles including any antibody-virus complexes, if present, from the sample-antibody mixture using the second nanopillar array; and detecting the antibody-virus complexes, if present, in the particles using the diode-induced fluorescence detector.

A more complete understanding of the present invention, as well as further features and advantages of the present invention, will be obtained by reference to the following detailed description and drawings.

BRIEF DESCRIPTION OF THE DRAWINGS

FIG. 3a is a schematic diagram of a nanopillar array illustrating the array parameters $\theta_{max}$, G, and pillar pitch, $\lambda$ according to an embodiment of the present invention;

FIG. 3b is a scanning electron microscope (SEM) image of a sorting array according to an embodiment of the present invention;

FIG. 3c is a table showing the nanopillar array gap sizes G and measured percentage maximum angle P in nanopillar arrays, for a given particle diameter $D_P$, at flow velocities between 200-350 μm/s according to an embodiment of the present invention;

FIG. 3d is an image illustrating lateral displacement modes for zigzag, partial, and bumping according to an embodiment of the present invention;

FIG. 3e are SEM images of inlet and outlet regions bordering the array according to an embodiment of the present invention;

FIG. 3f are fluorescence microscopy images of fluorescent polystyrene beads flowing into the inlet region (top row) and exiting the array outlet region (bottom row), corresponding to those shown in the SEM images in FIG. 3e. according to an embodiment of the present invention;

FIG. 4a is a schematic diagram of an H1N1 viral particle with fluorescence detection scheme according to an embodiment of the present invention;

FIG. 4b is a composite fluorescence microscopy image showing displacement of H1N1 viral particles in a nanoscale deterministic lateral displacement array according to an embodiment of the present invention;

FIG. 4c is a histogram of percentage maximum angle across the outlet of the array shown in FIG. 4b according to an embodiment of the present invention;

FIG. 4d is a schematic diagram of a human placental exosome with fluorescence detection scheme according to an embodiment of the present invention;

FIG. 4e is a composite fluorescence microscopy image showing displacement of exosomes in a nanoscale deterministic lateral displacement array according to an embodiment of the present invention;

FIG. 4f is a histogram of percentage maximum angle across the outlet of the array shown in FIG. 4e according to an embodiment of the present invention;

FIG. 5a are fluorescence image mosaics of double stranded DNA (dsDNA) displacement in a deterministic lateral displacement array according to an embodiment of the present invention;

FIG. 5b are normalized fluorescence intensity line profiles of displaced DNA taken at the outlet of each array according to an embodiment of the present invention;

FIG. 5c is a diagram illustrating the percentage maximum angle of dsDNA as a function of DNA length according to an embodiment of the present invention;

FIG. 6a is an image of fluidic chips printed on a wafer according to an embodiment of the present invention;

FIG. 6b is an optical image showing microfluidic channels joined by nanochannel features, including pillar sorting arrays, according to an embodiment of the present invention;

FIG. 6c is a Fast Fourier Transform (FFT) confirming successful patterning of the design angle $\theta_t$ according to an embodiment of the present invention;

FIG. 6d is an SEM image of a sorting array according to an embodiment of the present invention;

FIG. 7a is an SEM image of $D_P$=110 nm beads according to an embodiment of the present invention;

FIG. 7b is an SEM image of $D_P$=50 nm beads according to an embodiment of the present invention;

FIG. 7c is an SEM image of $D_P$=20 nm beads according to an embodiment of the present invention;

FIG. 7d is a histogram of bead diameters measured from the SEM images in FIGS. 7a-c according to an embodiment of the present invention;

FIG. 7e is a table of properties of the bead samples according to an embodiment of the present invention;

FIG. 8a is a schematic diagram of an exemplary custom fluid jig according to an embodiment of the present invention;

FIG. 8b is a top-down image of the custom fluid jig with a nanoscale deterministic lateral displacement chip loaded according to an embodiment of the present invention;

FIG. 9a is a schematic diagram of a nanoscale deterministic lateral diffusion array showing particle flux entering from left (inlet) to right (outlet) according to an embodiment of the present invention;

FIG. 9b is a diagram of a plot of fluorescent line profiles taken at the outlet of arrays for a complete displacement scenario according to an embodiment of the present invention;

FIG. 9c is a diagram of a plot of fluorescent line profiles taken at the outlet of arrays for a partial displacement scenario according to an embodiment of the present invention;

FIG. 10 is a diagram illustrating polystyrene fluorescent bead displacement as a function of particle diameter compared to critical diameter needed for displacement in a parabolic flow according to an embodiment of the present invention;

FIG. 13a is a fluorescent microscopy image of the trajectory of an exosome through the nanoscale deterministic lateral displacement array particle according to an embodiment of the present invention;

FIG. 13b is a diagram illustrating collection of single-particle exosome trajectories taken at the outlet of a G=235 nm array according to an embodiment of the present invention;

FIG. 13c is a histogram of single-particle positions at the outlet according to an embodiment of the present invention;

FIG. 14a is an image of viral particle experimental controls which illustrates that virus alone shows no fluorescence according to an embodiment of the present invention;

FIG. 14b is an image of viral particle experimental controls which illustrates that antibodies alone follow the streamlines of the laminar flow according to an embodiment of the present invention;

FIG. 14c is an image of viral particle experimental controls which illustrates that anti-H1N1 antibody-virus complexes are bumped according to an embodiment of the present invention;

FIG. 14d is an image of viral particle experimental controls which illustrates that non-specific M13 antibodies do not bind viral particles and therefore do not bump according to an embodiment of the present invention; and FIG. 15 is a table of end-to-end coil diameters and scaling ratios calculated for dsDNA in nanoscale deterministic lateral displacement experiments according to an embodiment of the present invention.

DETAILED DESCRIPTION OF PREFERRED EMBODIMENTS

Figure 1:
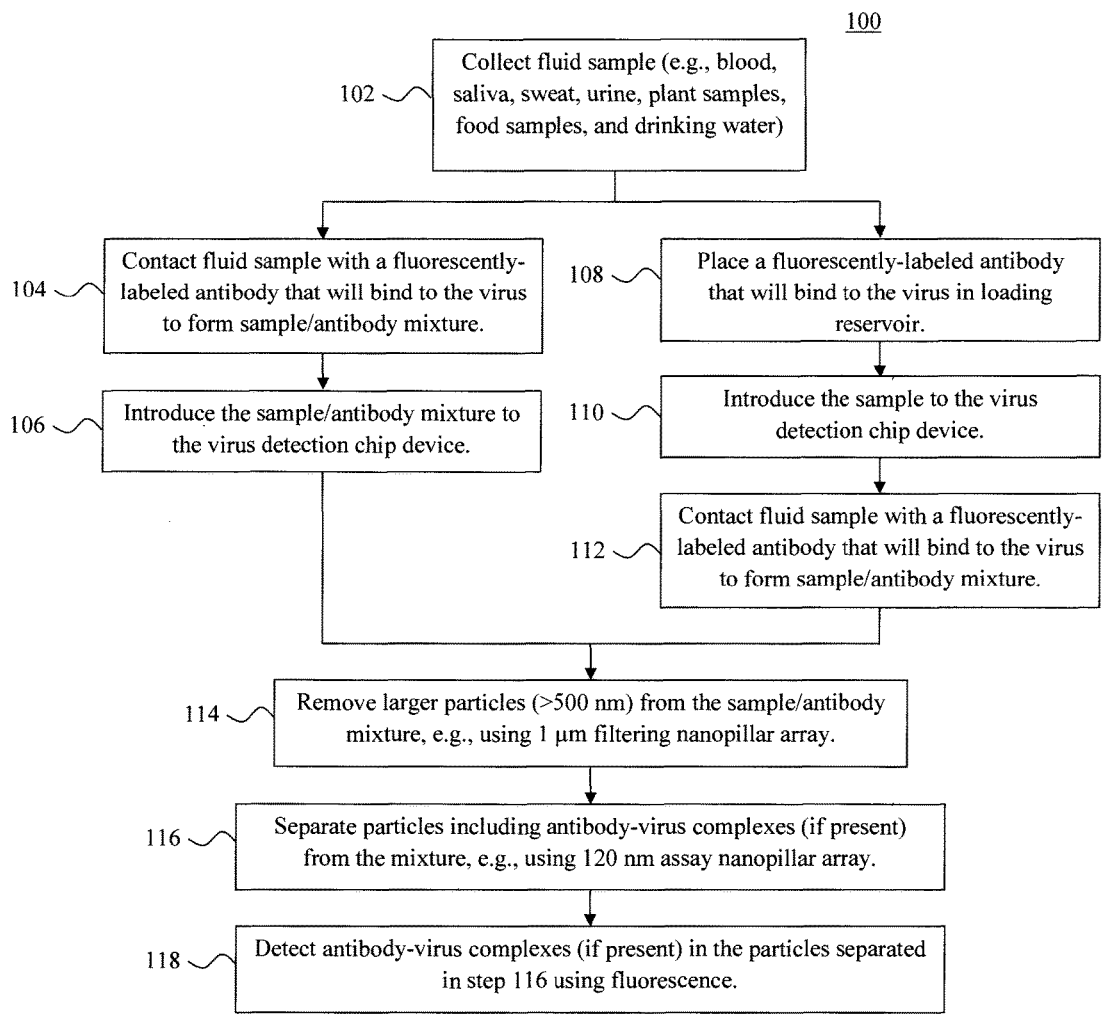
FIG. 1 is a diagram illustrating an exemplary methodology for virus detection according to an embodiment of the present invention.

Provided herein are nanotechnology-based techniques for sensitive, quantitative detection of viral particles from biological samples (e.g., blood, saliva, sweat, urine, plant samples, food samples, and drinking water) using antibodies against viral antigens in a rapid point-of-care protocol. Advantageously, the present techniques are carried out via a one-step system (thus simplifying the detection process), which could be self-administered and require only a small biological sample, similar to glucose monitoring systems used by diabetics.

Namely, as will be described in detail below, the present techniques utilize a silicon (Si) nanotechnology-based approach to identify fluorescently-labeled antibodies bound to viral particles in a biological sample, allowing for the detection of virus in a patient. A small-volume of sample (blood, saliva, sweat, etc.) would be incubated with a fluorescently-labeled antibody against the suspected virus. The mixed sample is applied to a diagnostic silicon chip (lab-on-a-chip (LOC)) device which uses an array of nanopillars to sort biomolecules based on size. Unbound antibodies are too small to be sorted and flow through the chip, while antibodies bound to virus are above the size threshold and are sorted. These sorted particles can be detected and quantified directly by fluorescence microscopy, e.g., by a fluorimeter or by an on-chip diode-induced fluorescence detector.

The primary advantages of the present virus detection chip over current viral detection methods include: smaller sample volume, lack of requirement for sophisticated laboratory equipment, portability, self-administration by an untrained individual, adaptability to any virus with an available antibody, and early detection capabilities. As described above, current viral detection technologies include enzyme-linked immunosorbent assay (ELISA) and polymerase chain reaction (PCR). Both of these techniques require well-equipped laboratories and trained technicians and can take hours to days to produce results, making them unsuitable for point-of-care diagnosis.

The present virus detection chip device is compact and compatible with on-chip detection technology making it highly portable. It requires less than 100 uL of sample volume and could be implemented in a manner similar to glucose monitoring kits for diabetics, making self-administration by a patient possible. The present virus detection relies on a fluorescent signal from an antibody to a specific virus. As antibodies exist for most viral capsids or envelopes, it is possible to design a chip to test for the presence of virtually any virus. Further the detection protocol described herein is not limited to human samples, but could also be used to detect plant and animal viruses provided antibodies are available.

Finally, many conventional virus detection tests rely on the production of viral antibodies in the patient, which occurs later in disease progression. The present techniques are sensitive enough to detect a small number of viral particles directly and could be used to determine an infection early in progression.

The present techniques are now described in detail by way of reference to methodology 100 of FIG. 1. In step 102, a fluid sample is collected. In general, fluid samples can be collected from virtually any virus-bearing source. This includes, but is not limited to, blood, saliva, sweat, plant tissue, drinking water, and food products. According to an exemplary embodiment, less than 100 microliters (µl) (e.g., from about 50 µl to about 100 µl, and ranges therebetween) is all that is needed to be collected for testing, since only a small amount of the fluid sample needs to be introduced to the capillary opening of the present (disposable) virus detection chip device (see below).

Non-blood samples could be collected at the point-of-care or in the field for rapid testing. Blood samples could also be produced quickly using a disposable lancet at the point-of care. This test could be used for any virus in the 100 nanometer (nm) size range, or larger, that has antibodies available for binding to the outer capsid or envelope of the virus. This includes, but is not limited to influenza viruses, adenoviruses, Ebola and Marburg viruses, poxviruses (including small pox), and herpes viruses (including Epstein-Barr virus and Varicella-zoster virus).

The fluid sample collected in step 102, is then prepared for analysis. It is notable however that only minimal sample preparation is needed, and most of the preparative steps can (if so desired) be built into the virus detection chip device itself. In general, to prepare the sample for analysis, the sample is contacted (i.e., mixed) with a fluorescently-labeled antibody that will bind to the virus capsid or envelope.

A variety of fluorescent tags could be used and include, but are not limited to, quantum dots, Alexa Fluors® (available from Life Technologies™, Grand Island, N.Y.), fluorescein, rhodamine, Oregon green, pyrene, and HiLyte™ Fluor dyes (available from AnaSpec, Inc., Fremont, Calif.). Antibodies will be conjugated to these fluorescent tags using covalent linkages including, but not limited to, amino, carboxyl, thiol, and azide chemistries.

According to an exemplary embodiment, the sample preparation is carried out by first mixing the fluid sample with a solution containing the fluorescently-labeled antibody. See step 104. The sample/antibody mixture can then be introduced to the capillary opening of the virus detection chip device in step 106.

The present virus detection chip device, however, can have a built-in loading reservoir (see below) in which the tagged antibody can be lyophilized/dried on the chip so that there is no mixing required for the sample to be loaded on the chip—i.e., the sample simply gets loaded and mixes on chip with the antibody. This alternative embodiment where the sample preparation steps are built into the chip itself simplifies the assay process, which can be beneficial for point-of-care access to the present techniques.

By way of example only, to pre-load the chip with tagged antibody at least one picogram of antibody is lyophilized in the loading reservoir of the chip. See step 108. This amount of antibody is in excess of the virus and will ensure that each viral particle can be bound by several antibodies assuming a viral load of over 10,000 copies/milliliter. Of course, lower viral loads can also be detected, but will simply be bound my more antibodies until each virus is saturated by bound antibody.

In step 110, the sample (collected in step 102) is introduced to the capillary opening of the present virus detection chip device. A sample buffer of phosphate-buffered saline (PBS, 10 millimolar (mM) sodium phosphate, 18 mM potassium phosphate, 137 mM sodium chloride, 2.7 mM potassium phosphate) is preferably loaded behind the sample to ensure that the entire sample enters the array. Following flow through the capillary opening the sample will enter the loading reservoir, where it will mix and bind with the antibody (step 112) prior to entering the filtration and pillar arrays. With whichever procedure is implemented, i.e., either premixing the sample with a tagged antibody solution (steps 104-106) or passing the sample through the tagged antibody via the loading reservoir of the chip (steps 108-112), a mixture containing the sample and tagged antibody is now present within the virus detection chip device.

As will be described in detail below, the virus detection chip device employed herein contains an array of nanopillars, through which the sample/antibody mixture will pass, which will serve to separate (by size) antibody-virus complexes present in the sample/antibody mixture. Thus, this nanopillar array may also be referred to herein as an "assay nanopillar array."

The sample/antibody mixture might also contain larger particles (e.g., particles with dimensions greater than 500 nm), such as organelles, cell membrane, and protein aggregates. These larger particles can clog the assay nanopillar array, and thus it is desirable to remove them from the sample before the sample passes through the assay nanopillar array. See step 114. Therefore, the virus detection chip device preferably contains another array of nanopillars (also referred to herein as a "filtering nanopillar array") before the assay nanopillar array which serves to filter out (i.e., remove) these larger particles from the sample. Namely, the sample/antibody mixture passes first through the filtering nanopillar array wherein particles larger than 500 nm are removed. The sample then passes through the assay nanopillar array wherein antibody-virus complexes, if present, are separated out from the mixture. See step 116. The filtering nanopillar array and the assay nanopillar array may also be referred to herein as a "first" and a "second" nanopillar array, respectively. Further, as will be described in detail below, the filtering nanopillar array and the assay nanopillar array differ generally in the size/spacing of the nanopillars in the array.

The filtering and assay nanopillar arrays implemented herein are, what is known in the art as, deterministic lateral displacement pillar arrays. Deterministic lateral displacement pillar arrays in silicon have proven an efficient technology to sort, separate, and enrich micrometer-scale particles. See, for example, Huang et al., "Continuous Particle Separation Through Deterministic Lateral Displacement," Science, vol. 304 (May 2004) (hereinafter "Huang"); Inglis, et al., "Critical particle size for fractionation by deterministic lateral displacement," Lab Chip, 6, 655-658 (March 2006) (hereinafter "Inglis"); and Loutherback et al., "Improved performance of deterministic lateral displacement arrays with triangular posts," Microfluid Nanofluid 9:1143-1149 (May 2010), the contents of each of which are incorporated by reference as if fully set forth herein. However, deterministic lateral displacement pillar array technology has never been translated to the nanoscale.

According to an exemplary embodiment, the filtering nanopillar array is a 1 micrometer (μm) gap (between the pillars) nanopillar array which sorts particles larger than 500 nm in size and "bumps" them to the right side of the array. The principles behind the mechanism of bumping are described, for example, in Huang and Inglis. The size of particles sorted is dependent on the ratio of the spacing between the nanopillars and the size of the nanopillars themselves. These larger particles will be sorted in step 114 by the filtering nanopillar array into a waste reservoir on the right side of the chip (see below).

After removal of large particles, the sample will enter the assay nanopillar array (e.g., a 120 nm nanopillar array) which will separate antibody-virus complexes, if present, from the mixture. See step 116. Namely, all particles in the mixture that are larger than about 100 nm will be sorted by the assay nanopillar array and bumped to the right, including the virus bound by the fluorescent antibody.

In step 118, fluorescence can then be used to detect whether or not antibody-virus complexes are present in the particles retrieved in step 116. Again, this detection functionality can be built directly into the chip. For example, particles that exit the right side of the assay nanopillar array (see above) can be collected in an on-chip diode-induced fluorescence detector, which can detect and quantify fluorescent signal from the fluorescently labeled antibody-virus complex. Any signal detected above a pre-calibrated threshold will indicate the presence of virus in the sample. Any background particles larger than 100 nm that enter the 120 nm assay nanopillar array will not affect detection as they will not be fluorescently labeled and will not produce a signal.

In a sample lacking the virus detected by the antibody, the antibody alone will not be deflected by the assay nanopillar array. Antibodies consist of two large and two small chains which total 160 kilo-Daltons in molecular weight. Assuming a globular shape, each unbound antibody would have an estimated size of less than 10 nm, and would flow straight through the 120 nm assay nanopillar array rather than being bumped to the right. Therefore, no fluorescent signal will be collected or detected by the diode-induced fluorescence detector as all of the fluorescently-labeled antibodies will flow out the bottom of the chip.

Figure 2:
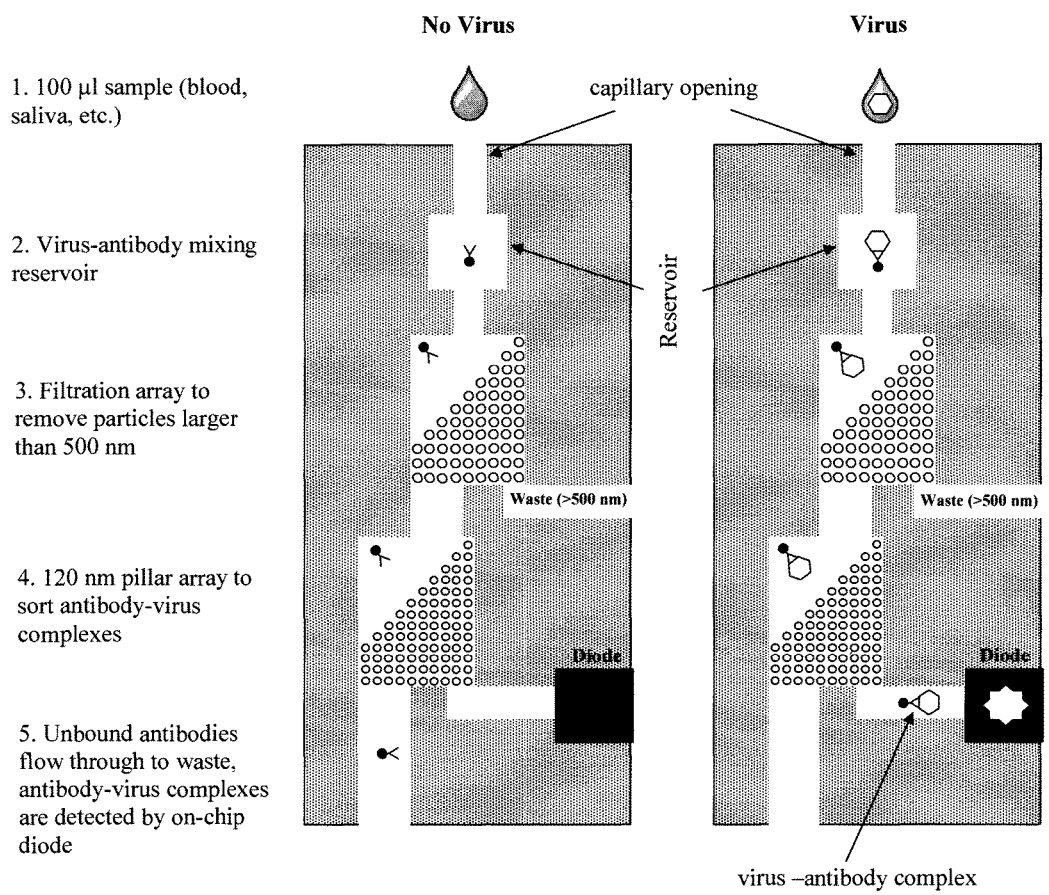
FIG. 2 is a schematic diagram illustrating use of the present virus detection chip device in performing the methodology of FIG. 1 according to an embodiment of the present invention.

FIG. 2 is a schematic diagram illustrating use of the above-described (disposable) virus detection chip device in performing methodology 100 of FIG. 1. For illustrative purposes, a scenario where the sample does not contain the virus is shown on the left side of the figure and a scenario where the sample contains the virus is shown on the right side of the figure. A fluid sample first must be collected. As described above, the fluid sample used herein can be collected from any virus-bearing source, such as blood, saliva, sweat, plant tissue, drinking water, and food products. Further, only a small amount of the fluid sample is needed for testing, for example, less than 100 μl (e.g., from about 50 μl to about 100 μl, and ranges therebetween)—see above. The presence of the virus in the right hand sample is indicated using a multi-faceted polygon (i.e., to represent the virus capsid).

As described above, the fluid sample can (optionally) be premixed with a fluorescently-tagged antibody solution or, as shown in FIG. 2, lyophilized/dried tagged antibody can be placed in the mixing reservoir of the chip. In the latter case, the sample itself can be collected by the capillary opening of the chip. The capillary opening is connected to the mixing reservoir. Thus, from the capillary opening, the sample will flow through the mixing reservoir where the tagged antibody will bind to the virus, if present, in the sample. The result is a sample-antibody mixture. As shown in FIG. 2, in the case where the virus is not present in the sample (example shown on the left) the mixing reservoir will contain no virus-antibody complexes (i.e., all that is shown in the mixing reservoir in the "No Virus" scenario is the fluorescent tagged antibody). On the other hand, in the case where the virus is present in the sample (example shown on the right) the mixing reservoir will contain virus-antibody complexes (i.e., virus-antibody complexes are shown in the mixing reservoir in the "Virus" scenario).

As provided above, a sample buffer (e.g., PBS) can be loaded behind the sample to ensure that all of the sample enters the nanopillar arrays. Namely, the mixing reservoir is connected to the (first) filtering nanopillar array. As provided above, the filtering array serves to remove larger particles from the sample-antibody mixture that can potentially clog the smaller assay nanopillar array. As shown in FIG. 2, the particles filtered out of the mixture by the filtering nanopillar array are sent off as waste (labeled "Waste (>500 nm)") through a conduit off to the right side of the chip.

The mixture then moves to the (second) assay nanopillar array which, as shown in FIG. 2, is connected to the (first) filtering nanopillar array. As provided above, the assay nanopillar array will separate antibody-virus complexes, if present, from the mixture. Namely, all particles in the solution that are larger than about 100 nm will be sorted by the assay nanopillar array and bumped to the right, including the virus bound by the fluorescent antibody. Thus, as shown in FIG. 2, in the case where the virus is not present in the sample (example shown on the left) no virus-antibody complexes are present, and as such no virus-antibody complexes are bumped (i.e., separated out) by the assay nanopillar array. It is notable that the mixture might in fact contain particles (other than virus-antibody complexes) that might get separated out at this stage (and which are not shown in FIG. 2). However, these particles will not be fluorescently tagged, and thus will not contribute to the detection carried out at the diode (i.e., as shown in FIG. 2 unbound tagged antibodies will pass through the chip as waste). On the other hand, in the case where the virus is present in the sample (example shown on the right) virus-antibody complexes are present and will be bumped (i.e., separated out) by the assay nanopillar array. See virus-antibody complex directed (via the assay nanopillar array) to the conduit leading to the diode-induced fluorescence detector (labeled "Diode").

Finally, the diode-induced fluorescence detector which, as shown in FIG. 2, is used to detect and quantify the presence of virus-antibody complexes in the particles separated out by the assay nanopillar array—due to the presence of the fluorescent tags. As provided above, any signal detected above a pre-calibrated threshold can be used to indicate the presence of virus in the sample. Any background particles larger than 100 nm that enter the 120 nm assay nanopillar array will not affect detection as they will not be fluorescently labeled and will not produce a signal.

The present nanopillar array-based techniques can be used to rapidly sort biological entities down to 20 nm in continuous flow, using nanoliter volumes, with single-particle resolution. Thus, in addition to viruses, the present techniques open the possibility for sorting a wide range of biological entities, setting the foundation for novel applications in single-cell fractionation, proteomics and point-of-care medical diagnostics. For example, the ability to sort exosomes, secreted lipid vesicles with sizes between 30 nm to 120 nm containing a protein and nucleic acid cellular snapshot have been demonstrated in accordance with the present techniques. The ability to sort exosomes based on size and surface markers is important to future medical applications, and suggests the viability of sorting a variety of lipid membrane based particles such as synaptic vesicles. Further, separation of double stranded DNA (dsDNA) fragments by length at the single molecule level has been demonstrated in accordance with the present techniques, which has broad applications in genomic sequencing and epigenetics.

One important parameter in the study of deterministic lateral displacement pillar arrays is the Peclet number, defined as the ratio of the time for a particle to diffuse a characteristic distance d in the system to that required to advect the same distance, which decreases rapidly as the feature size decreases at fixed fluid speed. The Peclet number is proportional to d and the fluid speed. The concern for particle sorting in deterministic lateral displacement is that at too low a Peclet number, diffusion will overwhelm the displacement process and the motion will no longer be deterministic. Therefore one goal herein is to determine the behavior of deterministic lateral displacement at the nanoscale. In this regard, the trajectories of fluorescent polystyrene beads with (particle) diameters $D_P$=20-110 nm in a deterministic lateral displacement pillar array were studied. The nanoparticle experiments allowed not only for an analysis of heretofore unexplored scales for deterministic lateral displacement, but also to calibrate and interpret the results of experiments with exosomes (which have similar diameters) to be discussed later.

A full description of the design parameters and the nature of the particle trajectories in the deterministic lateral displacement sorting technology has been previously described, for example, in Huang. Briefly, the pillar pitch λ, the row-to-row shift δ, and the gap size between pillars G, (FIG. 3a) define a critical diameter $D_C$. FIGS. 3a-f illustrate nanoscale deterministic lateral displacement sorting using pillar array chips with gap size G ranging from 25-235 nm and maximum angle $\theta_{max}$=5.7 degrees. At the microscale, particles with diameter $D_P$>$D_C$ will be laterally displaced across an array in "bumping" mode, with a maximum angle $\theta_{max}$ (FIG. 3a) defined by the geometry of the array as $\tan(\theta_{max})=\delta\lambda^{-1}$. Particles with diameter $D_P$ below $D_C$ follow the direction of laminar flow in "zigzag" mode, and thus the overall direction of the trajectory is the same as the laminar flow, with a mean angle of zero with respect to the array. In order to study the properties of nanoscale deterministic lateral displacement, arrays were fabricated with gap sizes as small as 25 nm (FIG. 3b). Additional description of the fabrication details are provided below.

FIG. 3c shows the capability of the present nanoscale deterministic lateral displacement arrays to displace particles down to 20 nm in diameter using 42 nm gaps. A transitional mode was found between bumping ($\theta=\theta_{max}$) and zigzag ($\theta$=0), which is referred to herein as "partial displacement mode" where $0<\theta<\theta_{max}$ and is represented by the percentage maximum angle $P=\theta\theta_{max}^{-1}\times100$. As seen in FIG. 3c, partial displacement occurs for 50 nm beads going from G=235 nm to 118 nm. This demonstrates that particles of different particle diameter $D_P$ will display different θ for a given G. The efficiency of the displacement process can be calculated from $\eta=\tan(\theta)/\tan(\theta_{max})$ (see FIG. 12—described below). For the small migration angles obtained, this approximates to $\eta\sim\theta\theta_{max}^{-1}=P/100$, so the percentage maximum angle roughly describes the efficiency of sorting in the array. The partial displacement mode can be viewed then as a lower efficiency bumping mode.

To explore the sorting capability of deterministic lateral displacement arrays at the nanoscale, a series of monodisperse fluorescence polymer beads were tested in arrays of gap size G=42 nm, 118 nm, 134 nm, 214 nm, and 235 nm, using the design shown in FIG. 3a. Each particle solution was introduced across the entire width of the array inlet and particle displacement was observed using epifluorescence microscopy. The array width, W=36 μm, and length, L=360 μm, were chosen according to criteria borrowed from the microscale, such that a particle with diameter above $D_C$ that enters the array at the top left point of the inlet (see leftmost panel in FIG. 3d) would exit the array at the bottom right point of the outlet, following a maximum angle $\theta_{max}$=5.7 degrees. This maximum angle was chosen because it combines a relatively large integer value of row shift repeats (N=10) and high displacement efficiency (see Inglis). It has been shown that $D_C$ decreases with N, and therefore the larger N is, the smaller the diameters of particles that could be displaced with maximum angle θ for a given G (see Huang and Inglis). When lateral displacement occurs, the particle density moves towards the collection wall along the length of the array, generating a fluorescent, triangular pattern with a migration angle, θ (FIG. 3d). This permits imaging populations of smaller particles that cannot be tracked individually (especially for $D_P$<50 nm).

FIG. 3d is an optical microscope image, 20× magnification, of an exemplary nanoscale deterministic lateral displacement device (labeled "nanoDLD array"), showing the overall configuration of the array. FIG. 3e provides scanning electron microscope (SEM) images of inlet and outlet regions bordering the array. FIG. 3f provides fluorescence microscopy images of fluorescent polystyrene beads flowing into the inlet region (top row) and exiting the array outlet region (bottom row), corresponding to those shown in the SEM images in FIG. 3e. The lateral displacement modes for zigzag, partial, and bumping are shown for $D_P$=20 nm/G=214 nm, $D_P$=50 nm/G=134 nm, and $D_P$=110 nm/G=235 nm, respectively. The migration angle θ, indicates the lateral displacement of the particle flux in the array.

In T. Kulrattanarak et al. "Analysis of mixed motion in deterministic rachets via experiment and particle simulation," Microfluid Nanofluid 10:843-853 (2011) (hereinafter "Kulrattanarak"), the contents of which are incorporated by reference as if fully set forth herein, displacement angles in between 0 and $\theta_{max}$ were observed, and it was concluded that this mixed motion between zigzag and bumping was due to the anisotropic permeability of the arrays. While this effect can still apply to nanoscale deterministic lateral displacement arrays, the low Peclet number regime makes the two systems rather different, and diffusion is likely the dominant effect.

Comparison of polystyrene bead displacement with the theoretical critical diameter (as determined by Inglis) shows that for particle diameter $D_P$=50-110 nm, the onset of the bumping mode is in agreement with the existing model. At the row-shift fraction ε=0.10 used in the present arrays, Inglis predicts a theoretical critical diameter $D_C$=0.37 G, whereas complete displacement was obtained herein at ~0.4-0.47 G, which is in agreement with the experimental observations in Inglis. The transition across the theoretical critical diameter in accordance with the present techniques is smoother than the abrupt transition observed for deterministic lateral displacement at the microscale, consistent with a mixed motion or partial displacement mode (see Kulrattanarak). In contrast to the larger beads, 20 nm beads only deflect roughly 32% of the maximum angle. For G=42 nm and $D_P$=20 nm, the Peclet number Pe is Pe~0.58, assuming an average flow of 300 μm·s$^{-1}$ and a particle diffusivity of D=21.9 μm$^2$·s$^{-1}$. This small Pe value implies that the beads are diffusing across the streamlines, even within a single row shift. This suggests a limit has been approached at which the deterministic lateral displacement enters a regime that deviates from the mode of operation at the microscale. Even though at small Peclet numbers nanoscale deterministic lateral displacement is not strictly deterministic, the fact that the displacement angle is not zero has usefulness in potential sorting of nanoscale colloids. In practical applications, any partially displacing particle can be fully displaced by increasing the length of the array. A full-displacement length $L_C$, can be defined for a given θ and W, at which a partially displaced sample will completely laterally displace (see FIG. 12—described below). This implies that partial displacement can be used to make arrays that act as "prisms"; splitting a distribution of particles sizes into different angles that can be collected sequentially down the array. The advantage of this is that only a single gap size G is needed to fractionate a band of particle sizes.

The dimensions of nanoscale deterministic lateral displacement arrays are compatible with the scales of biological entities ranging from viruses to small protein aggregates. After demonstrating the possibility of partial displacement—even at low Peclet numbers, biological colloids were tested with calibrated fluorescent beads to demonstrate the applicability of nanoscale deterministic lateral displacement to biological systems. Many nanoscale bio-colloids exhibit spherical morphology and would be expected to show similar displacement behavior as polymer beads, based on the physics nanoscale deterministic lateral displacement technology. The present system was tested on monodisperse H1N1 influenza virus and polydisperse human placental mesenchymal stem cell (MSC) derived exosomes. H1N1 influenza A virus has a spherical virion of $D_P$=100 nm. See FIG. 4a—which is a schematic diagram of an H1N1 viral particle of 100 nm diameter with fluorescence detection scheme. Exosomes display a range of particle sizes, $D_P$~10 s-100 s nm. See FIG. 4d—which is a schematic diagram of a human placental exosome with fluorescence detection scheme. Here, the migration angle of deactivated H1N1 viral particles and human placental mesenchymal stem cell (MSC) derived exosomes were compared to the fluorescent bead calibration results displayed in FIG. 3c (described above).

H1N1 virus was labeled with a fluorescent antibody and introduced into a G=214 nm array. In the virus free control, the fluorescent antibodies, which are approximately 10 nm in diameter, exhibited a zigzag mode behavior with θ=0 (see FIG. 14b—described below). Displacement of antibody-virus complexes was observed at θ=$\theta_{max}$=5.7° (see FIG. 4b), as expected for a $D_P$~100-120 nm particle. See FIG. 4b—which is a composite fluorescence microscopy image showing displacement of H1N1 viral particles labeled with an Alexa-488-tagged α-N1 antibody in the G=214 nm array. This suggests that viral particles perform similarly to polystyrene beads in the nanoscale deterministic lateral displacement array. FIG. 4c is a histogram of percentage maximum angle across the outlet of the array shown in FIG. 4b.

In contrast, when MSC exosomes are introduced into a G=235 nm array, a dispersion of migration angles is observed. See FIGS. 4e and 4f. FIG. 4e is a Composite fluorescence microscopy image showing displacement of fluorescently labeled exosomes in a G=235 nm array and FIG. 4f is a histogram of percentage maximum angle across the outlet of the array shown in FIG. 4e. Based on the polystyrene bead size calibration, the exosome population can be related to three diameter ranges. Exosomes were visualized using a lipid-bound fluorescent dye which incorporates into the vesicle membrane and does not affect their diameters $D_P$. Assuming the exosomes behave like the polystyrene beads, from the calibration data it was calculated that 1.5% of the exosome population has $D_P$>110 nm, 56.3% of the population is between 50 nm<$D_P$<110 nm, and 42.2% of the population has $D_P$<50 nm. See FIG. 4f. Of this latter population, 69.2% have P>0. Negative P values are due to particles with trajectories that carry them away from the collection wall, against the asymmetry of the array. Since these trajectories are deviations greater than even a zigzag mode, they may be due to a higher diffusion coefficient for these smaller particles causing randomized percolation through the array. The binning of exosome sizes is meant to guide the eye to show the potential for fractioning exosomes; it is expected that each size exhibits a distribution of migration angles (due at least in part to diffusion) and therefore the different size populations may overlap to some degree. The comparison implies that fractions of exosome sizes could be collected by selectively channeling off particles from the array, opening the potential for probing exosome biochemistry as a function of particle size. Exosomes with $D_P$ up to 600 nm would be expected for the samples tested; however, particles greater than the gap size, G=235 nm, are filtered out upstream to reduce clogging in the array.

Deterministic lateral displacement arrays have been primarily applied to spherical particles, but there is also interest in sorting polymers, particularly biopolymers such as nucleic acids, by size. Polymers coil into a compact globular state and it is of interest to understand how this state behaves in nanoscale deterministic lateral displacement arrays. In that regard, varying lengths of dsDNA, labeled with YOYO-1 fluorescent dye, were tested in G=235 nm nanoscale deterministic lateral displacement arrays. As in the case of polystyrene beads, a partial displacement mode was observed. The migration angle θ, varies as a function of dsDNA length, appearing to saturate at P=100% around 4 kb.

FIGS. 5a-c are diagrams illustrating DNA displacement in the present nanoscale deterministic lateral displacement array. Namely, FIG. 5a are fluorescence image mosaics of 0.5-48.5 kb double stranded DNA (dsDNA) displacing in a G=235 nm array. FIG. 5b are normalized fluorescence intensity line profiles of displaced DNA taken at the outlet (dotted white line in FIG. 5a) of each array. Circles are used in FIG. 5b to denote the inflection point at which the migration angle was measured. FIG. 5c is a diagram illustrating the percentage maximum angle of dsDNA as a function of DNA length.

As the length of the dsDNA molecules are comparable to the dimensions of the array, a De Gennes model was used to calculate the confined end-to-end coil diameter, $2R_{DG}$ (see FIG. 15—described below). A description of the De Gennes model is provided, for example, in M. Daoud et al., "Statistics of Macromolecular Solutions Trapped in Small Pores," Journal de Physiques, 38 (1), pp. 85-93 (January 1977), the contents of which are incorporated by reference as if fully set forth herein. For the calculation, a persistent length of 50 nm was used for YOYO-1-stained dsDNA. Comparing with the expected critical diameter, $D_C$=87 nm, it was seen that 1.0 kb dsDNA has $2R_{DG}$=74 nm, so one would expect to see roughly 50% dsDNA bumping and more than that above this chain length, which is what is observed from the displacement experiments. This would suggest that the displacement condition can be predicted for the dsDNA, assuming the molecule forms a "particle" of $D_P$~$2R_{DG}$. Although the onset of bumping is close to the expected critical diameter, only at 4.0 kb, where $2R_{DG}$~295 nm, complete displacement (i.e., bumping mode) was obtained, thus showing that dsDNA exhibits the same partial displacement behavior as seen in the fluorescent beads. For the two smallest DNA molecules tested, 250 and 500 base-pairs (bp), the molecular length is smaller than the gap size, so the de Gennes model does not apply. However, collectively these results demonstrate the ability to fractionate dsDNA by size.

In summary, these experiments demonstrate a breakthrough in the application of deterministic lateral displacement technology at the nanoscale. Manufacturable silicon processes were used to produce nanoDLD arrays of highly uniform gap sizes, ranging from 25-235 nm. These processes are compatible with complementary metal oxide semiconductor (CMOS) integration, allowing focus on the next challenge of integrating digital logic with nanofluidic devices. Using fluorescent nanoparticles it is demonstrated herein that even at Peclet numbers of order 1, where diffusion and deterministic displacement compete, nanoDLD arrays can be used to separate particles based on size. Finally, proof of principle of size-based separation of exosomes, viruses and DNA has been shown herein. The nanoDLD array constitutes a building block in a new generation of on-chip fluidic processing technologies that could potentially be multiplexed to produce improved on-chip diagnostics.

A description of the array and particle preparation, as well as further details on the analysis of the nanoscale deterministic lateral displacement fluorescence images is now provided Fluidic Chip and Pillar Array Fabrication:

Nanofluidic chips were fabricated on 200 mm wafers to enable high-quality fluorescence imaging of nanoscale polymer beads and bio-colloids when coupled with a custom fluidic jig as described, for example, in Wang et al., "Hydrodynamics of Diamond-Shaped Gradient Nanopillar Arrays for Effective DNA translocation into Nanochannels," ACS NANO, vol. 9, no. 2, pp. 1206-1218 (January 2015) (hereinafter "Wang"), the contents of which are incorporated by reference as if fully set forth herein. See FIG. 6a—which is an image of these fluidic chips printed on a 200 nm wafer using mixed mid-ultraviolet (MUV) and electron beam (e-beam) lithography. Optical contact lithography followed by a combination of e-beam and deep-ultra violet (DUV) lithography schemes (see, for example, Wang et al., "200 nm Wafer-Scale Integration of Sub-20 nm Sacrificial Nanofluidic Channels for Manipulating and Imaging Single DNA Molecules," 2013 IEEE International Electron Devices Meeting (IEDM) (December 2013), the contents of which are incorporated by reference as if fully set forth herein) were utilized consecutively to define microchannel and nanofluidic pillar array features, respectively, in an silicon dioxide ($SiO_2$) hard mask on bulk silicon substrates. See FIG. 6b. Following hard mask definition, all features were transferred into silicon in tandem using a reactive-ion etch (RIE).

40×40 mm square fluidic chips (12 per wafer) were fabricated on 200 mm Si wafers with a blanket layer of thermal oxide ranging from 100-150 nm. Oxide thickness was selected depending on the target depth of the silicon etch corresponding to a particular pillar height. An optical contact lithography SUSS MA8 mask aligner was used to print microchannel features in a photoresist mask, which was subsequently etched into $SiO_2$ with an etch stop on the Si bulk using RIE (See FIG. 6a).

After defining microchannels in the $SiO_2$ hard mask, a negative-tone, e-beam lithography strategy was employed to provide the sharpest possible resolution of the nanofluidic pillar array features, connecting sets of microchannels (see FIG. 6b), and a positive DUV-defined lithography window was used to mask the remainder of the wafer outside the nanofluidic pillar array region from RIE processing when defining these features in the thermal oxide hardmask. E-beam lithography was performed on a high-resolution VectorBeam 6 (Leica VB6HR) system to define pillar arrays in a resist stack consisting of an HM8006 organic planarization layer (OPL) (JSR) coated with a thin 2% hydrogen silsesquioxane (HSQ) (Dow Corning) negative tone e-beam resist. After developing the exposed features, the wafers were coated with a 0.45 µm-thick positive photoresist and DUV window regions were printed directly on top of the e-beam resist features using a 0.65 NA DUV stepper (ASML) (see FIG. 6b). RIE was then used to transfer the e-beam features into the thermal oxide hard mask and stop on Si after which all resist was stripped in an oxygen ($O_2$) plasma asher (GaSonics).

With all features defined in the $SiO_2$ hard mask, RIE was used to simultaneously etch the pillar array and microchannel features into silicon. Optimized RIE processing was carried out in an DPSII ICP etch chamber (Applied Materials, CA) for pattern transfer to fabricate 200-450 nm high Si pillars from the e-beam resist pattern, depending on the desired gap width. First, the negative-tone HSQ resist was used to etch through the OPL using an $N_2/O_2/Ar/C_2H_4$ chemistry at 400 watts (W) source power, 100 W bias power, and 4 millitorr (mTorr) pressure at 65° C. The $SiO_2$ hard mask was then patterned using $CF_4/CHF_3$ chemistry at 500 W source power, 100 W bias power, and 30 mTorr pressure at 65° C.

Next, the OPL carbon resist was stripped using $O_2/N_2$ chemistry in an Axiom downstream asher (Applied Materials, CA) at 250° C. Finally, using the $SiO_2$ hard mask, Si features defining the arrays and microchannels were etched using the DPS II ICP etch system (Applied Materials, CA) by first a $CF_4/C_2H_4$ breakthrough step and then $Cl_2/HBr/CF_4/He/O_2/C_2H_4$ main etch at 650 W source power, 85 W bias power, and 4 mTorr pressure at 65° C. Final chip preparation required stripping the hard mask oxide and regrowing a thin thermal oxide layer ranging from 10-50 nm.

Nanoscale Deterministic Lateral Displacement Chip Preparation:

To produce a functioning nanoscale deterministic lateral displacement (nanoDLD) device from the fabricated array chips, a glass coverslip was bonded over the array to provide a water-tight enclosure. Chips were bonded as reported in Wang, using the same coverslip design. Bonded chips were annealed at 550° C. for 7 hours in a convection oven (Lindberg/Blue), and stored in a nitrogen dry box until needed. In some cases, bonded chips were further surface functionalized prior to experiments; (see below). Bonded chips were used in experiments within 2 weeks of annealing.

Deterministic Lateral Displacement Chips Wetting Protocol:

To run a deterministic lateral displacement experiment on a bonded chip, the arrays needed to be wetted with fluid. Chips were set vertically in a custom glass holder, with inlets below outlets. The chips were submerged in enough ethanol (200 proof, Pharmco-AAPER) so that only the inlet ports were covered, while the outlet ports remained open to air to allow proper wetting. The ethanol was allowed to capillary wet each fluidic array entirely (~10-30 min). The chips were then transferred to diH2O (Millipore) and fully submerged for 60 minutes. At this stage chips can be kept in water until needed for experiments without evidence of de-wetting.

Surface Modification of Nanoscale Deterministic Lateral Displacement Devices:

For running bio-colloids (i.e., viral particles, exosomes, and dsDNA) it was determined that surface modification of the array silica was needed in order to prevent sample adhesion to the device surfaces. Bio-colloids, especially exosomes, when run in unmodified chips would clog the micro-array inlet and would not reach the array.

For surface modification, a chip was immediately transferred from the oven, after annealing, to a 500 milliliter (mL) glass, cylindrical, flat flange reactor (Wilmad-LabGlass). The chip was positioned upside down (inlets down) on a custom glass holder such that a stir bar could operate beneath the chip. The reactor was sealed with a 3-neck head, and purged with nitrogen flow for 30 minutes Via cannula, 250 mL of a 10 millimolar (mM) solution of 2-(methoxypoly (ethyleneoxy)6-9propyl)dimethylchlorosilane (technical grade, 90%, Gelest Inc.) dissolved in degassed, anhydrous chloroform (Sigma Aldrich), was added to the reactor. The liquid level submerged only the inlet holes of the chip, allowing capillary action to wick solvent up into the arrays. Care was taken not to splash and wet the outlet ports of the chip while loading the reagent, as this leads to bubbles, and unmodified regions in the device. The chip was allowed to sit for 16 hours at room temperature, under nitrogen, with gentle stirring. The chip was then removed and transferred into 300 mL ethanol (200 proof, Pharmco-AAPER) and stirred for 16 hours. This process was repeated for $diH_2O$ (Millipore). At this stage, chips could be kept in water until needed for experiments. Chips have been kept up to 1 month submerged before running successfully.

Particle Sample Preparation:

Polystyrene Beads:

Aqueous, fluorescent polystyrene beads, with carboxylic functional groups were purchased from commercial suppliers, with particle diameters $D_P$=20 nm (Molecular Probes, Life Technologies, Thermo Fisher Scientific, Inc.), 50 nm and 110 nm (Bangs Laboratories, Inc.). All beads have absorption bands compatible with 488 nm excitation, and emission at 510-520 nm. Bead samples to be run in arrays were prepared by diluting the as supplied bead solutions in TE buffer (BioUltra, for molecular biology, pH 7.4, Sigma Aldrich) with 3% v/vtotal 2-mercaptoethanol (Sigma Aldrich), to inhibit photo-oxidation, and 2-10% v/vtotal Tween20 (For molecular biology, Sigma Aldrich), to prevent particle aggregation and clogging. Typically a sample solution of 200 µL was prepared.

FIGS. 7a-e show the physical properties of the beads used in experiments. Namely, FIGS. 7a-c are SEM images of $D_P$=110 nm, 50 nm, and 20 nm, respectively, beads coated with a layer of evaporated Ti/Au (1 nm/10 nm). The scale bars shown represent 200 nm. FIG. 7d is a histogram of bead diameters measured from the SEM images in FIGS. 7a-c. FIG. 7e is a table of properties of the bead samples used in the nanoscale deterministic lateral displacement experiments. a: Mean diameter±standard deviation.

Bead solutions were momentarily vortexed to mix, and then centrifuged at 3000 revolutions per minute (RPM) for about 30 seconds. Bead solutions were prepared fresh daily for each experiment. Prior to use, 5 microliters (µL) of solution were set between two glass microslides and imaged to visually verify the quality of the beads solution.

Exosomes:

Placental mesenchymal stem cell (MSC) derived exosomes were obtained from Zen-Bio, Inc. Mean particle diameter is <DP>=290 nm, 100 μg, 165 μL, 0.60 mg·mL-1, 9.5·108 particles·mL-1. Particles were purchased labeled with DiO lipophilic cyanine dye (484 nm excitation, 501 nm emission). The as-obtained material was split into 10×, ~15 μL aliquots and frozen at −80° C. until needed. Prior to running an experiment, an aliquot was removed from cold storage and allowed to thaw at 4° C. for 30 minutes. The sample was then vortexed momentarily and then centrifuged at 3000 RPM for about 30 seconds to recollect. The sample was directly loaded into the flow chamber on the fluid jig.

Viral Particle Preparation:

Monoclonal antibodies against H1N1 neuraminindase (Sigma, SAB3500064) and M13 [E1] (Abcam, ab24229) were labeled with AlexaR-488 on primary amines (Life Technologies). 33 nanomolar (nM) inactivated influenza viral particles (AFLURIA, bioCSL, 2014-2015) were incubated with 2.2 nM fluorescent antibody for 30 minutes at 4° C. in a solution of 14 mM NaCl, 0.5 mM Na2HPO4, 20 nM KH2PO4, 160 nM KCl, and 2 mM CaCl2. 15 μL of sample was introduced to a 212 nm gap array.

DNA Sample Preparation:

Stock solutions of 0.5-20 kb DNA and λ-DNA (0.5 μg/μL, New England Biolabs) were diluted to 100 μg/μL in 10 mM TE buffer (10 mM Tris, 1 mM EDTA, pH 8, Life Technologies) with 3% 2-mercaptoethanol and 0.1% TWEEN 20. DNA was labeled with YOYO-1 iodide fluorescent dye (491/509 nm) (Life Technologies) at a DNA base pair-to-dye ratio of 5:1. Samples were incubated at room temperature for 2 hours, and stored at 20° C. for use.

Running Nanoscale Deterministic Lateral Displacement Particle Displacement Experiments:

Bonded and wetted chips were used for running displacement experiments. A chip was loaded into a custom built fluid jig. See FIGS. 8a-b. FIG. 8a is a schematic diagram of the fluid jig, and FIG. 8b is a top-down image of the fluid jig with a nanoscale deterministic lateral displacement chip loaded. In the example depicted in FIG. 8b, twelve threaded ports (six inlets and six outlets) are shown. The rectangular window, through which the microscope objective can reach the chip to image, can be seen in the middle of the jig.

As shown in FIG. 8a, the fluid jig is composed of a mounting base and a connector plate into/through which high-pressure liquid chromatography (HPLC) fittings can be screwed to inject fluid samples. The connector plate has a rectangular window designed to allow up to a 100× oil-immersion objective (Zeiss N-Achroplan 100×/1.25 oil, Zeiss, Germany) to be used for fluorescence imaging. The sample is loaded into the inlet reservoir of the connector plate, and the plate then screwed down onto to the chip/mounting base. A syringe pump (QMixx, Cetoni GmBH, Germany) is connected to the inlet port of the connector plate. The 10 mL syringe+tubing is filled with diH$_2$O (Millipore). Imaging is carried out on a Zeiss Scope.A1 upright fluorescence microscope coupled with an Andor iXon Ultra 897 (Andor Technology Ltd., Oxford Instruments, UK) EMCCD camera connected to a computer, where both imaging and pump pressure are controlled. A 470 nm light emitting diode LED was used for excitation, with the Zeiss filter set 38 HE (470/40 excitation, 495 beam splitter, 525/50 emission).

Array Structures:

Fast Fourier transform (FFT) analysis of the arrays (see FIG. 6c) confirmed a maximum angle θmax, of 5.8° which is very close to the design value of 5.7°. The maximum angle θmax=5.7° was chosen as it corresponds to a relatively small row shift fraction c=0.1 leading to a well-defined row repeat N=10, where θmax=tan$^{-1}$ (ε) and N=1/ε$^2$. Having a precise N simplifies design criteria while a small c increases the efficiency of a particular gap size in sorting the smallest possible particle, since the critical diameter Dc to sort a particle in the parabolic flow model is given by Dc=2αGε with α being a scaling factor depending on the flow profile. This sorting efficiency becomes crucial to induce sorting of very small entities such as proteins, particularly as gaps are scaled in the tens of nanometers regime, pushing the limits of fabrication and ability to effectively wet these features.

FIG. 6d shows the cross-sectional SEM image of a G=134 nm pillar array with pillar pitch λ=400 nm. Gap scaling and uniformity is demonstrated through RIE optimization and thermal oxidation of the Si posts, permitting well-controlled gap widths. Gap sizes for each array tested were determined by randomly measuring 3 sets of 5 adjacent gaps across the ~35 μm width of the pillar arrays (a statistical average of 15 gaps per array), including 1 set chosen near the array center and the other 2 sets nearer to each edge of the array. Gap variation from pillar top to bottom was minor but not negligible so measurements were taken at pillar mid-height as indicated by the dotted line in FIG. 6d. Thermal oxidation after pillar etching on parallel-processed wafers permitted controllable means of tuning of the gap size to effectively narrow the gap to a desired width based on the results from an SEM cross-section of a send-ahead wafer for each array fabricated.

General Experimental Layout:

When running a sample, a syringe pump is used to control the pressure to obtain a stream flow at 200-300 μm s-1. In typical experiments it requires 10-30 min for particles to reach the array from the connector plate inlet. Video images are collected of particle flux across the inlet of the array to assess the degree of particle distribution prior to injection into the array, and across the outlet to capture the degree of displacement at the end of the process. Exposure time is 17.9 ms, 200 frames per video. For each combination of gap size G and particle diameter DP, three or more independent experiments (individual arrays) were run.

In the case of exosomes, a different fluid jig was used (see Wang) which uses negative pressure through vacuum to drive the fluid flow. An exosome sample was directly loaded into the inlet fluidic reservoir of the flow chamber and a ~1 torr vacuum applied to the pump connector on the outlet side of the jig.

Analysis of Nanoscale Deterministic Lateral Diffusion Fluorescence Microscopy Images for Particle Behavior:

Analysis of Fluorescent Polystyrene Bead Displacement:

Fluorescence image videos of the array outlet are analyzed using custom software to determine the migration angle of the displaced particle flux. In the current array configuration, the flux of particles across the array is displaced towards the collection wall, forming a fluorescent, triangular pattern (white triangle in FIG. 9a). A depletion region, where particles have been displaced out, appears on the opposite side of the array from the collection wall (dark triangle in FIG. 9a). The extent of this depletion region at the outlet of the array determines the lateral displacement ΔW, of the particle flux. Determination of the lateral displacement is complicated by the fact that the edge of the particle flux, seen in the cross-section of fluorescence intensity across the array outlet, has a continuous form with no sharp cut-off. The "edge" of the particle flux is estimated, and thus $\Delta W$, using the inflection point of the fluorescence intensity (FIG. 9b). This assumes that the fluorescent intensity distribution corresponds to the particle density distribution. As shown in FIG. 9a, particles are displaced upwards towards the collection wall of the array, forming a fluorescent triangle pattern (wedge), from which the migration angle $\theta$, and lateral displace, $\Delta W$, can be measured. The lateral displacement is taken at the outlet of the array. In the schematic, the particles are completely displacing (bumping mode) so $\theta = \theta_{max} = 5.7°$, the maximum angle of the arrays used in this work. In FIGS. 9b and 9c, the dashed lines show the 1st derivative of the fluorescent line profiles, indicating the inflection point (black dot). The lateral displacement, $\Delta W$, is taken as the distance between the left-most wall of the array (opposite the collection wall) and the inflection point. Using the length of the array, L, and the lateral displacement, $\Delta W$, the migration angle can be calculated from $\tan(\theta) = \Delta W/L$. The line which is the 1st derivative taken before a 50-point smooth of the data (dashed line) is labeled in FIG. 9c.

The migration angle $\theta$, is defined as $\tan(\theta) = \Delta W\ L^{-1}$, where L is the length of the array. For a completely displaced particle sample, all particles end up at the collection wall at the end of the array, and $\theta = \theta_{max} = 5.7°$, the maximum angle of the array. For no displacement, the particle flux covers the entire outlet, and $\theta = 0$. The displacement efficiency is defined as:

$$\eta = \frac{\Delta W}{W} = \frac{\tan\theta}{\tan\theta_{max}} \sim \frac{\theta}{\theta_{max}} = \frac{P}{100}$$

To compare the effectiveness of sorting particles for a given DP and G, a figure of merit, FOM, is defined as the ratio between the lateral displacement of the particles, and the distance needed to fully displace the particles across the array:

FOM=tan $\theta$=$\eta$ tan $\theta_{max}$

From the definition of the figure of merit, the displacement length can be defined as:

$$L_C = \frac{W}{FOM}$$

FIG. 10 is a diagram illustrating polystyrene fluorescent bead displacement as a function of particle diameter, $D_P$, compared to critical diameter needed for displacement in a parabolic flow. Bead values are given for a given row shift fraction, $\varepsilon = 0.10$, and scaling ratio $D_P G^{-1}$. Value shading represents the percentage maximum angle, P. The black line is the calculated critical diameter scaling ratio, $D_C G^{-1} = 1.16\varepsilon^{0.5}$. Theoretically, beads with scaling ratios below the critical line should exhibit zigzag mode, P=0%, and not displace within the array, while those above should show complete displacement, P=100%.

Figures 11, 12:
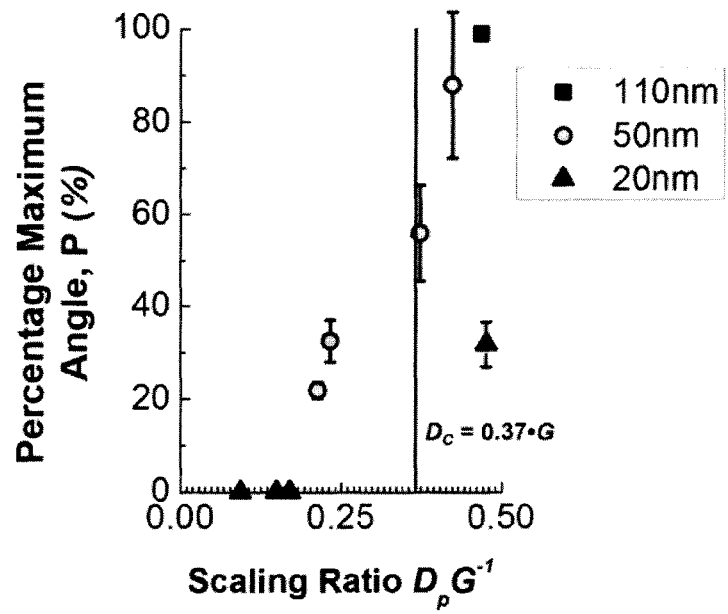
FIG. 11 is a diagram illustrating percentage maximum angle of fluorescent polystyrene beads displaced in nanoscale deterministic lateral displacement arrays as a function of the scaling ratio between particle diameter and gap size according to an embodiment of the present invention.
FIG. 12 is a table of performance parameters for nanoscale deterministic lateral displacement of fluorescence polystyrene beads according to an embodiment of the present invention.

FIG. 11 is a diagram illustrating percentage maximum angle of fluorescent polystyrene beads displaced in nanoscale deterministic lateral displacement arrays as a function of the scaling ratio between particle diameter and gap size. Bead diameters are 110 nm (squares), 50 nm (circles) and 20 nm (triangles). Error bars represent the standard deviation of at least three independent experiments. The line at $D_P G^{-1} = 0.37$ represents the theoretical critical diameter, $D_C$, in parabolic fluid flow at which beads are expected to be in bumping mode. P=100% corresponds to complete displacement of beads (bumping mode), P=0% corresponds to no displacement (zigzag mode), and 0%<P<100% indicates partial displacement mode.

FIG. 12 is a table of performance parameters for nanoscale deterministic lateral displacement of fluorescence polystyrene beads.

Analysis of Exosome and Virus Displacement:

For exosomes and viral particles, single-particle trajectories are recorded in fluorescence microscope images, instead of a flux density, as in the case of fluorescent polystyrene beads. This means that a distribution of single-particle events were obtained, instead of a continuous distribution determined by the average fluorescence density. In general, flowing particles form a streak or "trace" in a given video frame. For each particle observed, the location of the head of the particle's trace is manually marked per frame of video. The collection of x,y-coordinate pairs taken from the combined number of frames (typically 200) defines the trajectory of the particle within the image frame of the video (see FIGS. 13a-c).

The migration angle $\theta$, is defined as $\tan(\theta) = \Delta X/\Delta Y$, with $\Delta X = _{xfinal-xinitial}$ and $\Delta Y = _{yfinal-yinitial}$, using the initial and final x,y-coordinates of the particle trajectory. In determining $\theta$, only trajectories that initiate at a distance larger than 10% of the array width from the collection wall are used, in order to avoid the possibility of miscounting particles that are partially displacing as ones which are bumping. The value of 10% of W comes from analysis of the half-width at half-maximum of the 110 nm bead fluorescence intensity against the collection wall, which shows complete bumping mode. From the collected $\theta$ of all the single-particle trajectories, a histogram of the percentage maximum angle P, can be generated. This distribution of angles is equivalent to the fluorescence intensity line profiles used in the bead analysis, however it is acquired from the accumulation of single-particle data rather than the measurement of an ensemble fluorescence.

FIG. 13a is a fluorescent microscopy image of an exosome particle. A series of 6 images, taken every 36 milliseconds, overlaid together shows the trajectory of the particle through the nanoscale deterministic lateral displacement array. The particle appears as a small line (trace) due to the finite exposure time (18 milliseconds). Scale bar represents 10 µm. The single-particle trajectory can be measured from the movement of the head of the trace through the array as a function of time. FIG. 13b illustrates collection of single-particle exosome trajectories taken at the outlet of a G=235 nm array. Traces in dotted white line initiated within 10% of the array width from the collection wall and are not used for determining migration angle, while those in black initiate outside this threshold. FIG. 13c is a histogram of single-particle positions at the outlet (black horizontal line in FIG. 13b). Values in dotted white line and black correspond to those in FIG. 13b. The migration angle can be calculated from the amount of lateral displacement (x-position) of the particle from the start of the trajectory, and the length of distance travelled (y-position, FIG. 13b).

Control samples of H1N1 virus alone and fluorescently labeled anti-H1N1 antibody alone were run through the array. See FIGS. 14a-c. Additionally, a non-H1N1 virus binding fluorescently labeled anti-M13 antibody with virus was run through the array. This demonstrates that bumping mode is only observed when both virus and a specific antibody are present.

Specifically, FIGS. 14a-d are images of viral particle experimental controls—i.e., representative composite fluorescent microscope image of Alexa Fluor® 488-labeled anti-H1N1 neuraminidase and M13 antibodies and inactivated influenza viral particles in a 212 nm gap array functionalized with a polyethylene glycol silane ligand. Direction of flow is from top to bottom with particles migrating towards the collection wall on the right of the image. The image is composed of sequential frames showing antibody-virus complex trajectory (frame time=18 ms). Virus alone shows no fluorescence (see FIG. 14*a*). Antibodies alone follow the streamlines of the laminar flow (see FIG. 14*b*) while anti-H1N1 antibody-virus complexes are bumped (see FIG. 14*c*). Non-specific M13 antibodies do not bind viral particles and therefore do not bump (see FIG. 14*d*).

Analysis of dsDNA Displacement:

dsDNA experiments were analyzed using the same methods as fluorescent polystyrene beads (see above). The de Gennes mean confined coil radius was calculated using:

$$R_{DG} = Nh\frac{(wp)^{1/3}}{D^{2/3}}$$

With persistence length, p=50 nm, molecular width, w=2.4 nm, length per base, h=0.34 nm, number of bases per strand, N, and geometric average of nanochannel taken as $D=(GH)^{1/2}=307$ nm, with nanopillar gap size G=235 nm and gap height H=400 nm.

FIG. 15 is a table of end-to-end coil diameters and scaling ratios calculated for dsDNA in nanoscale deterministic lateral displacement experiments.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method for virus detection, comprising the steps of:

collecting a fluid sample from a virus-bearing source;

contacting the fluid sample with an antibody that binds to viruses to form a sample-antibody mixture, wherein the antibody is labeled with a fluorescent tag;

separating particles including any antibody-virus complexes, if present, from the sample-antibody mixture using an assay nanopillar array, wherein gap sizing between nanopillars in the assay nanopillar array separates the particles by bumping the particles toward a conduit leading to a detector off to one side of the assay nanopillar array, with a remainder of the sample-antibody mixture including unbound antibody labeled with the fluorescent tag passing straight through the assay nanopillar array as waste thereby permitting a continuous flow of the fluid sample through the assay nanopillar array, wherein the assay nanopillar array separates particles that are larger than 100 nanometers from the sample-antibody mixture;

removing particles larger than 500 nanometers from the sample-antibody mixture using a filtering nanopillar array prior to the separating step to prevent the particles larger than 500 nanometers from entering and clogging the assay nanopillar array, wherein gap sizing between nanopillars in the filtering nanopillar array removes the particles larger than 500 nanometers by bumping the particles larger than 500 nanometers toward a waste conduit off to one side of the filtering nanopillar array; and detecting the antibody-virus complexes, if present, in the particles from the separating step by detecting fluorescence from the fluorescent tag.

2. The method of claim 1, wherein the virus-bearing source is selected from the group consisting of: blood, saliva, sweat, plant tissue, drinking water, and food products.

3. The method of claim 1, wherein the fluorescent tag is selected from the group consisting of: quantum dots, Alexa Fluors®, fluorescein, rhodamine, Oregon green, pyrene, and HiLyte™ Fluor dyes.

4. The method of claim 1, wherein the gap sizing between the nanopillars in the assay nanopillar array is about 120 nanometers.

5. The method of claim 1, wherein the gap sizing between the nanopillars in the filtering nanopillar array is about 1 micrometer.

6. The method of claim 1, wherein the step of contacting the fluid sample with the antibody comprises the step of:

mixing the fluid sample with a solution containing the antibody labeled with the fluorescent tag.

7. The method of claim 1, further comprising the step of:

placing the antibody labeled with the fluorescent tag in a mixing reservoir.

8. The method of claim 7, wherein the step of contacting the fluid sample with the antibody comprises the step of:

passing the fluid sample through the mixing reservoir whereby the fluid sample contacts the antibody.

9. The method of claim 1, wherein the antibody-virus complexes, if present, in the particles are detected using the detector.

10. The method of claim 1, wherein an amount of the fluid sample collected is from about 50 microliters to about 100 microliters, and ranges therebetween.

11. A chip-based immunoassay method, comprising the steps of:

providing a virus detection chip device having: a capillary opening; a mixing reservoir connected to the capillary opening; a first nanopillar array connected to the mixing reservoir; a second nanopillar array connected to the first nanopillar array; and a detector connected to the second nanopillar array;

introducing a fluid sample collected from a virus-bearing source to the virus detection chip device through the capillary opening;

in the mixing reservoir, contacting the fluid sample with an antibody that binds to viruses, wherein the antibody is labeled with a fluorescent tag to form a sample-antibody mixture;

removing particles larger than 500 nanometers from the sample-antibody mixture using the first nanopillar array to prevent the particles larger than 500 nanometers from entering and clogging the second nanopillar array, wherein gap sizing between nanopillars in the first nanopillar array removes the particles larger than 500 nanometers by bumping the particles larger than 500 nanometers toward a waste conduit off to one side of the first nanopillar array;

separating particles that are larger than 100 nanometers including any antibody-virus complexes, if present, from the sample-antibody mixture using the second nanopillar array, wherein gap sizing between nanopillars in the second nanopillar array separates the particles that are larger than 100 nanometers by bumping the particles that are larger than 100 nanometers toward a conduit leading to the detector off to one side of the second nanopillar array, with a remainder of the sample-antibody mixture including unbound antibody labeled with the fluorescent tag passing straight through the second nanopillar array as waste thereby permitting a continuous flow of the fluid sample through the second nanopillar array; and detecting the antibody-virus complexes, if present, in the particles using the detector.

12. The method of claim 11, wherein the virus-bearing source is selected from the group consisting of: blood, saliva, sweat, plant tissue, drinking water, and food products.

13. The method of claim 11, wherein the gap sizing between the nanopillars in the first nanopillar array is about 1 micrometer.

14. The method of claim 11, wherein the gap sizing between the nanopillars in the second nanopillar array is about 120 nanometers.

* * * * *